(12) United States Patent
Walter et al.

(10) Patent No.: US 8,119,565 B2
(45) Date of Patent: Feb. 21, 2012

(54) HERBICIDAL CONTROL USING SULFENTRAZONE AND DITHIOPYR

(75) Inventors: James F. Walter, West Chester, PA (US); Frank Robert Walls, Jr., Goldsboro, NC (US)

(73) Assignee: FMC Corporation, Philadelphia, PA (US)

( * ) Notice: Subject to any disclaimer, the term of this patent is extended or adjusted under 35 U.S.C. 154(b) by 54 days.

(21) Appl. No.: 12/765,943

(22) Filed: Apr. 23, 2010

(65) Prior Publication Data

US 2010/0292081 A1 Nov. 18, 2010

Related U.S. Application Data

(60) Provisional application No. 61/178,325, filed on May 14, 2009.

(51) Int. Cl.
*A01N 43/40* (2006.01)
*A01N 43/653* (2006.01)

(52) U.S. Cl. ......... 504/139; 504/130; 504/244; 504/272

(58) Field of Classification Search .................. None
See application file for complete search history.

(56) References Cited

U.S. PATENT DOCUMENTS

2002/0004457 A1* 1/2002 Nevill et al. .................. 504/138

OTHER PUBLICATIONS

"Sulfentrazone Herbicide Fact Sheet", US Department of Energy Bonneville Power Administration, Dec. 2004.*
"Alligare—Dithiopyr 40 Specialty Herbicide Specimen Label", Sep. 2008.*
Boger, P and Wakabayashi, K. "Sulfentrazone" in "Peroxidizing Herbicides", 1999, p. 365.*

* cited by examiner

*Primary Examiner* — Ernst Arnold
*Assistant Examiner* — Christopher R Lea

(57) ABSTRACT

The present invention provides an herbicidal method for selective pre- and post-emergence control of broadleaf and grass weeds by applying a synergistic herbicidal composition, wherein the composition comprises a mixture of sulfentrazone and dithiopyr.

4 Claims, No Drawings

HERBICIDAL CONTROL USING SULFENTRAZONE AND DITHIOPYR

FIELD OF THE INVENTION

This invention relates to herbicidal methods for selective synergistic weed control by applying an herbicidal composition, wherein the composition consists of a mixture of N-[2,4-dichloro-5-[4-difluoromethyl-4,5-dihydro-3-methyl-5-oxo-1H-1,2,4-triazol-1-yl]phenyl]methanesulfonamide and S,S'-dimethyl 2-(difluoromethyl)-4-(2-methylpropyl)-6-(trifluoromethyl)-3,5-pyridinedicarbothiolate, to a locus where weeds are present or are expected to be present.

BACKGROUND OF THE INVENTION

The use of herbicides to control weeds in turf is well known. There are two types of herbicide applications, pre-emergence herbicides prevent weed seeds from germinating or emerging and post-emergence herbicides that kill emerged and actively growing plants.

Pre-emergence turf herbicides are generally more effective, but must be applied early in the season before annual weed seeds germinate. In order to provide season-long control most pre-emergent herbicides need to be reapplied six to eight weeks after the initial application.

Post-emergence turf herbicides are used to control weeds after germination and emergence from the soil. The benefit of using a post-emergence turf herbicide for weed control is that it is used only where an infestation is present.

It would be most beneficial to provide a pre- and post-emergence turf herbicide that provides synergistic control of weeds such as chickweed, clover, cudweed, parsley, dock, plantain, medic, dandelion, sorrel and crabgrass in one application without injury to turf grasses.

SUMMARY OF THE INVENTION

The present invention provides an herbicidal method for selective pre- and post-emergence control of broadleaf and grass weeds by applying a synergistic herbicidal composition, wherein the composition comprises a mixture of sulfentrazone and dithiopyr.

DETAILED DESCRIPTION OF THE INVENTION

The present invention provides a synergistic herbicidal composition, wherein the herbicidal composition comprises a mixture of sulfentrazone and dithiopyr, and methods of using the composition in turf sites. In particular, the synergistic herbicidal composition and methods of the present invention provide improved selective pre- or post-emergence control of broadleaf and grass weeds such as chickweed, clover, cudweed, parsley, dock, plantain, medic, dandelion, sorrel and crabgrass in one application without injury to turf grasses at rates which neither component alone can do.

Sulfentrazone is the common name for N-[2,4-dichloro-5-[4-difluoromethyl-4,5-dihydro-3-methyl-5-oxo-1H-1,2,4-triazol-1-yl]phenyl]methanesulfonamide, CAS registry number [122836-35-5]. Dithiopyr is the common name for S,S'-dimethyl 2-(difluoromethyl)-4-(2-methylpropyl)-6-(trifluoromethyl)-3,5-pyridinedicarbothiolate, CAS registry number [97886-45-8].

One aspect of the present invention provides a method for selective pre- and post-emergence synergistic control of broadleaf and grass weeds in a turf site, said method comprising applying the herbicidal composition in a ratio of from 1:1 to 1:4 (sulfentrazone to dithiopyr). A particular embodiment of the present invention is a method for synergistically controlling broadleaf and grass weeds in turf sites which comprises applying the individually formulated herbicides, either together or sequentially, to a locus where weeds are present or expected to be present.

The synergistically effective amount of the combination of sulfentrazone and dithiopyr may vary according to the weed pressure, application timing, weather conditions, mode of application, topographical character and the like. In general, a synergistic effect can be achieved at application rates of from 0.0625 lb/ac to 0.25 lb/ac of sulfentrazone in combination with from 0.125 lb/ac to 0.5 lb/ac of dithiopyr.

In particular, the present invention provides a method for selective synergistic control of broadleaf and grass weeds in a turf site, said method comprising applying an herbicidal composition comprising a mixture of sulfentrazone and dithiopyr in a ratio of from 1:1 to 1:4, at a rate of from 0.0625 lb/ac to 0.25 lb/ac of sulfentrazone in combination with from 0.125 lb/ac to 0.5 lb/ac of dithiopyr to a locus where weeds are present or are expected to be present.

The presence of a synergistic effect between the two active ingredients is established with the aid of the Colby equation (see Colby, S. R., "Calculating Synergistic and Antagonistic Responses of Herbicide Combinations", *Weeds* 1967, 15, pg 20-22): $E = X + Y - (XY/100)$.

Using the method of Colby, the presence of a synergistic interaction between two active ingredients is established by first calculating the expected activity, 'E', of the mixture based on activities of the two components applied alone. In the equation above, 'X' is the herbicidal activity in percentage control of sulfentrazone applied alone at rate 'x'. The 'Y' term is the herbicidal activity of dithiopyr applied alone at rate 'y'. The equation calculates 'E', the herbicidal activity of the mixture of 'X' at rate 'x' with 'Y' at rate 'y'. If 'E' is lower than the observed activity, synergy is present. If the herbicidal effects are strictly additive, and no interaction has occurred, 'E' will be equal to or higher than the observed activity.

The terms "weed" and "weeds" refer to any unwanted vegetation in turf sites. The terms "turf", "turf site" and "turf sites" refers to, but is not limited to, residential, public and institutional lawns, athletic fields, commercial sod farms and golf courses, including putting greens, fairways and roughs.

In addition, fertilizers and pesticides such as herbicides, fungicides and insecticides can be employed in conjunction with the herbicidal composition as described above, providing they do not adversely affect the interaction between the components of this invention.

The herbicidal composition of the present invention may be employed in many forms and is often most conveniently prepared in aqueous form immediately prior to use. One method of preparing such a composition is referred to as "tank mixing" in which the ingredients in their commercially available form, either with or without other additives, are mixed together by the user in a quantity of water.

In addition to tank mixing immediately prior to use, the herbicidal composition may be formulated into a more concentrated primary composition which is diluted with water or other diluent before use. Such compositions may comprise a surface active agent in addition to the active ingredients and examples of such compositions are set forth below.

The herbicidal composition of the present invention can be formulated as a granule of relatively large particle size for dry application to the site where control is desired (for example, 5/16 or 4/8 US Mesh), on fertilizer granules, as water-soluble or water-dispersible granules, as powdery dusts, as wettable powders, as emulsifiable concentrates, as aqueous emulsions, as solutions, or as any of the other known types of agriculturally-useful formulations, depending on the desired mode of application to the areas in which suppression of vegetation is desired. These formulations may contain as little as 0.1%, 0.2% or 0.5% to as much as 95% or more by weight of the total of the herbicide composition.

The herbicidal composition of the present invention can be in the form of a dispersible solution which comprises the herbicides dissolved in a water-miscible solvent with the addition of a dispersing agent.

Alternatively, the herbicidal composition of the present invention can be in the form of water-soluble or water-dispersible granules that disperse readily in water or other dispersant. Water-soluble or water-dispersible granules normally are prepared to contain about 5-80% of the herbicide composition, depending on the absorbency of the carrier, and usually also contain a wetting, dispersing or emulsifying agent to facilitate dispersion and may contain a preservative. Typical carriers for water-soluble or water-dispersible granules include Fuller's earth, natural clays, silicas, and other highly absorbent, readily wet inorganic diluents. For example, a useful water-soluble or water-dispersible granule formulation contains 26.71 parts of the herbicidal composition, 30.90 parts of ammonium sulfate, 30.89 parts of continental clay, 10.00 parts of sodium lignosulfonate as a dispersant, 1.00 part of sodium dioctylsuccinate as a wetting agent and 0.50 part of citric acid as a preservative. The mixture is milled, diluted with water to form a paste and the paste is extruded and dried to produce granules.

Other alternatives that may be employed are dusts which are free flowing admixtures of the herbicidal composition with finely divided solids such as talc, natural clays, kieselguhr, flours such as walnut shell and cottonseed flours, and other organic and inorganic solids which act as dispersants and carriers for the herbicides. These finely divided solids have an average particle size of less than about 50 microns. A typical dust formulation useful herein is one containing 1.0 part or less of the herbicidal composition and 99.0 parts of talc.

Also useful formulations for the herbicidal composition of the present invention are wettable powders in the form of finely divided particles that disperse readily in water or other dispersant. The wettable powder is ultimately applied to the locus where weed control is needed either as a dry dust or as an emulsion in water or other liquid. Typical carriers for wettable powders include Fuller's earth, kaolin clays, silicas, and other highly absorbent, readily wet inorganic diluents. Wettable powders are prepared to contain about 5-80% of the herbicide composition, depending on the absorbency of the carrier, and usually also contain a small amount of a wetting, dispersing or emulsifying agent to facilitate dispersion. For example, a useful wettable powder formulation contains 80.0 parts of the herbicidal composition, 17.9 parts of Palmetto clay, and 1.0 part of sodium lignosulfonate and 0.3 part of sulfonated aliphatic polyester as wetting agents. Additional wetting agents and/or oils will frequently be added to a tank mix to facilitate dispersion on the foliage of the plant.

Other useful formulations for the herbicidal composition of the present invention are emulsifiable concentrates (ECs) which are homogeneous liquid compositions dispersible in water or other dispersant, and may consist entirely of the herbicidal composition and a liquid or solid emulsifying agent, or may also contain a liquid carrier, such as xylene, heavy aromatic naphthas, isophorone, or other non-volatile organic solvents. For herbicidal application these concentrates are dispersed in water or other liquid carriers and applied as a spray to the area to be treated. The percentage by weight of the herbicidal composition may vary according to the manner in which the composition is to be applied, but in general comprises 0.5 to 95% of the herbicidal composition by weight of the total composition.

Suspension concentrate (SC) formulations may also be employed. These are similar to ECs, except that the herbicidal compounds are suspended in a liquid carrier, generally water. Suspension concentrate formulations, like ECs, may include small amounts of surfactants, emulsifiers, stabilizers, thickeners, antifoam agents and/or preservatives and will typically contain the herbicidal composition in the range of 0.5 to 95%, frequently from 10 to 50%, by weight of the total composition. For herbicidal application, SCs may be diluted in water or other liquid vehicle, for example, corn oil, kerosene, propylene glycol, or other suitable solvents, and are normally applied as a spray to the area to be treated.

Still other useful formulations for these herbicidal compositions include simple solutions of the herbicidal composition in a solvent in which it is completely soluble at the desired concentration, such as acetone, alkylated naphthalenes, xylene, or other organic solvents. Granular formulations, wherein the herbicides are carried on relative coarse particles, are of particular utility for application to turf sites by a spreader for penetration of grass or can be used in combination with a solid fertilizer to combine nutrition and weed control. Pressurized sprays, typically aerosols, wherein the herbicide composition is dispersed in finely divided form as a result of vaporization of a low-boiling dispersant solvent carrier may also be used.

In some circumstances it may be desirable to combine two types of formulation, e.g. one of the herbicidal compounds is used as an emulsifiable concentrate and the second herbicidal compound is dispersed as a powder in this concentrate.

The concentrate of the herbicidal composition (when used as the sole active components) in a composition for direct application to the locus where control is desired by conventional ground methods is preferably within the range of 0.001 to 10% by weight of the composition, especially 0.005 to 5% by weight, but more concentrated compositions containing up to 40% may be desirable.

Typical wetting, dispersing or emulsifying agents that may be used with the herbicidal composition of the present invention include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

In use on turf sites, the granular formulations, emulsifiable concentrates, flowable concentrates, aqueous emulsions, solutions, etc., may be diluted with water to give a concentration of the active ingredient in the range of 0.01% or 0.2% to 1.5% or 2.0%.

The following examples further illustrate the present invention, but, of course, should not be construed as in any way limiting its scope. The examples include protocols for the evaluation of the compositions of the present invention in which a beneficial effect was observed. The test compositions used were commercially available formulations of the test compounds. The following commercially available formulations were used: sulfentrazone, Dismiss™ Turf Herbicide from FMC Corporation; dithiopyr, DIMENSION® Ultra 40WP Specialty Herbicide from Dow AgroSciences LLC.

EXAMPLE 1

Pre-emergent Herbicidal Evaluation of Sulfentrazone, Dithiopyr and Mixtures Thereof Compositions of the present invention were tested for herbicidal efficacy in the following manner:

Test compositions containing sulfentrazone (Dismiss™ Turf Herbicide), dithiopyr (DIMENSION® Ultra 40WP Specialty Herbicide) and mixtures thereof, were diluted with water to provide the appropriate test rate concentrations.

The size of each experimental turf plot was 4 feet by 4 feet, treating the inner 10 ft$^2$ per plot. The application of each test composition was performed with a pressurized back-pack sprayer, calibrated to spray between 10 and 15 gallons per acre. Four replications were made for each test rate along an untreated control plot.

Control of large crabgrass (*Digitaria sanguinalis*), parsley piert (*Alchenilla arvensis*), common chickweed (*Stellaria media*) and shiny cudweed (*Gnaphalium spicatum*) was evaluated at 23 days after treatment (DAT) for each test rate. In order t to provide a measure of the effectiveness of a herbicide's performance weed control ratings were based on visual observations of the presence or absence of various weeds or of symptoms (necrosis, wilting, curling of leaves, discoloration etc.) on weeds compared to lack of symptoms. Ratings are based on the 0 to 100 rating system, where 0 equals no control and 100 equals complete control, which generally makes use of direct-percentage figures. In this system the standard basis for comparison is an untreated weedy check. Counts are made of each weed species found in the untreated area of the study. This provides a basis to give a precise representation of both weed infestation and degree of control provided by various chemical treatments. Counts are made on randomly selected areas which are generally 1 square foot to 1 square yard in size. Ratings are made for each weed species found in the untreated treatments. For example, a random area in an untreated plot has 10 yellow nutsedge plants per square foot equaling 0% control. A treated plot has only 1 yellow nutsedge plant found in the randomly selected area equaling 90% control.

There was no damage to the turf grass at any rate tested. The results are in Table 1 below. The Colby equation expected values are also in Table 1.

EXAMPLE 2

Post-emergent Herbicidal Evaluation of Sulfentrazone, Dithiopyr and Mixtures Thereof Compositions of the present invention were tested for herbicidal efficacy in the following manner:

Test compositions containing sulfentrazone (Dismiss™ Turf Herbicide), dithiopyr (DIMENSION® Ultra 40WP Specialty Herbicide) and mixtures thereof, were diluted with water to provide the appropriate test rate concentrations. A non-ionic surfactant (NIS) was added to each test solution, 0.25% V/V.

The size of each experimental turf plot was 4 feet by 4 feet, treating the inner 10 ft$^2$ per plot. The post-emergence application of each test composition was performed with a pressurized back-pack sprayer, calibrated to spray between 10 and 15 gallons per acre. Four replications were made for each test rate along an untreated control plot.

Control of broadleaf weeds was evaluated at 45 days after treatment (DAT) for each test rate. The broadleaf weeds included medic (*Medicago* sp.), buckhorn plantain (*Plantago lanceolata*), clover (*Trifolium* sp.), red sorrel (*Rumex acetosella*) and dandelion (*Traxacum afficinale*). Percent control of the broadleaf weeds was reported as a total number of broadleaf weeds controlled, not as individual species. The evaluation results were compared with results observed in untreated control plots in the same trials as described in Example 1 to determine % control and are summarized in Table 2 below. There was no damage to the turf grass at any rate tested. The Colby equation expected values are also in Table 2.

TABLE 2

Percent Control of Weeds With Post-emergent Applications of Sulfentrazone, Dithiopyr and Mixtures Thereof

| Treatment | Rate of application lb/ac | % Broadleaf Weed Cover | % Control of Broadleaf Weeds |
|---|---|---|---|
| Untreated Control | | 18 | 0 |
| Dithiopyr | 0.125. | 21 | 0 |
| | 0.25 | 8 | 55 |
| Sulfentrazone | 0.125 | 15 | 16 |
| | 0.25 | 10 | 44 |

TABLE 1

Percent Control of Weeds With Pre-emergent Applications of Sulfentrazone, Dithiopyr and Mixtures Thereof

| | | | % Control of Weeds | | | |
|---|---|---|---|---|---|---|
| Treatment | Rate of application lb/ac | | Large Crabgrass 132 DAT | Parsley Piert 23 DAT | Common Chickweed 23 DAT | Shiny Cudweed 23 DAT |
| Untreated Control | N/A | | 0 | 0 | 0 | 0 |
| Dithiopyr | 0.5 | | 88 | 38 | 53 | 29 |
| Sulfentrazone | .0125 | | 7 | 40 | 23 | 31 |
| | 0.25 | | 23 | 47 | 45 | 43 |
| Sulfentrazone + Dithiopyr | 0.125 + 0.5 | Observed | 95 | 80 | 93 | 91 |
| | 0.125 + 0.5 | Expected | 89 | 63 | 64 | 51 |
| | 0.25 + 0.5 | Observed | 90 | 82 | 87 | 90 |
| | 0.25 + 0.5 | Expected | 91 | 67 | 74 | 60 |

Highlighted numbers indicate synergistic herbicidal properties.

TABLE 2-continued

Percent Control of Weeds With Post-emergent Applications of Sulfentrazone, Dithiopyr and Mixtures Thereof

| Treatment | Rate of application lb/ac | | % Broadleaf Weed Cover | % Control of Broadleaf Weeds |
|---|---|---|---|---|
| Sulfentrazone + Dithiopyr | 0.125 + 0.25 | Observed | 6 | 66 |
| | 0.125 + 0.25 | Expected | | 62 |
| | 0.125 + 0.125 | Observed | 5 | 72 |
| | 0.125 + 0.125 | Expected | | 16 |

Highlighted numbers indicate synergistic herbicidal properties.

EXAMPLE 3

Pre- and Postemergent Herbicidal Evaluation of Sulfentrazone, Dithiopyr and Mixtures Thereof Compositions of the present invention were tested for herbicidal efficacy in the following manner:

Test compositions containing sulfentrazone (Dismiss™ Turf Herbicide), dithiopyr (DIMENSION® Ultra 40WP Specialty Herbicide) and mixtures thereof, were diluted with water to provide the appropriate test rate concentrations.

The size of each experimental turf plot was 4 feet by 4 feet, treating the inner 10 ft$^2$ per plot. The application of each test composition was performed with a pressurized back-pack sprayer, calibrated to spray between 10 and 15 gallons per acre. Four replications were made for each test rate along an untreated control plot.

Pre-emergence control of crabgrass (*Digitaria* sp.) was evaluated 180 days after treatment (DAT). Post-emergence control of curly dock (*Rumex crispus*) and shiny cudweed (*Gnaphalium spicatum*) parsley were evaluated at 65 days after treatment for each test rate. The evaluation results were compared with results observed in untreated control plots in the same trials as described in Example 1 to determine % control and are summarized in Table 3 below. There was no damage to the turf grass at any rate tested. The Colby equation expected values are also in Table 3.

EXAMPLE 4

Early Post-emergent Herbicidal Evaluation of Sulfentrazone, Dithiopyr and Mixtures Thereof Compositions of the present invention were tested for herbicidal efficacy in the following manner:

Test compositions containing sulfentrazone (Dismiss™ Turf Herbicide), dithiopyr (DIMENSION® Ultra 40WP Specialty Herbicide) and mixtures thereof, were diluted with water to provide the appropriate test rate concentrations. A non-ionic surfactant (X-77) was added to each test solution, 0.25% V/V.

The size of each experimental turf plot was 3 feet by 12 feet, treating the whole plot. The post-emergence application of each test composition was performed with a pressurized back-pack sprayer, calibrated to spray between 10 and 15 gallons per acre. The test compositions were applied when the emerging crabgrass was at the 1 to 4 leaf growth stage. Four replications were made for each test rate along an untreated control plot.

Control of crabgrass (*Digitaria* sp.) was evaluated at 45 days after treatment for each test rate. The evaluation results were compared with results observed in untreated control plots in the same trials as described in Example 1 to determine % control and are summarized in Table 4 below. There was no damage to the turf grass at any rate tested. The Colby equation expected values are also in Table 4.

TABLE 4

Percent Control of Crabgrass With Post-emergent Applications of Sulfentrazone, Dithiopyr and Mixtures Thereof

| Treatment | Rate of application lb/ac | % Control of Crabgrass |
|---|---|---|
| Untreated Control | | 0 |
| Dithiopyr | 0.25 | 50 |
| | 0.5 | 88 |

TABLE 3

Percent Control of Weeds With Pre-and Post-emergent Applications of Sulfentrazone, Dithiopyr and Mixtures Thereof

| | | | % Control of Weeds | | |
|---|---|---|---|---|---|
| Treatment | Rate of application lb/ac | | Crabgrass 180 DAT Pre-emergent application | Curly Dock 65 DAT Post-emergent application | Shiny Cudweed 65 DAT Post-emergent application |
| Untreated Control | N/A | | 0 | 0 | 0 |
| Dithiopyr | 0.0125 | | 59 | 36 | 53 |
| | 0.25 | | 23 | 60 | 60 |
| Sulfentrazone | 0.0625 | | 0 | 0 | 30 |
| | 0.125 | | 0 | 16 | 50 |
| | 0.25 | | 0 | 20 | 50 |
| Sulfentrazone + dithiopyr | 0.125 + 0.25 | Observed | 70 | 97 | 95 |
| | | Expected | 59 | 66 | 80 |
| | 0.125 + 0.125 | Observed | 70 | 50 | 90 |
| | | Expected | 23 | 46 | 77 |
| | 0.0625 + 0.125 | Observed | 38 | 47 | 87 |
| | | Expected | 23 | 36 | 67 |

Highlighted numbers indicate synergistic herbicidal properties.

TABLE 4-continued

Percent Control of Crabgrass With Post-emergent Applications of
Sulfentrazone, Dithiopyr and Mixtures Thereof

| Treatment | Rate of application lb/ac | | % Control of Crabgrass |
|---|---|---|---|
| Slufentrazone | 0.125 | | 30 |
| | 0.25 | | 36 |
| Sulfentrazone + Dithiopyr | 0.25 + 0.25 | Observed | 90 |
| | 0.125 + 0.25 | Expected | 68 |
| | 0.125 + 0.25 | Observed | 75 |
| | 0.125 + 0.25 | Expected | 65 |
| | 0.25 + 0.5 | Observed | 95 |
| | 0.25 + 0.5 | Expected | 92 |

Highlighted numbers indicate synergistic herbicidal properties.

Those of ordinary skill in the art will appreciate that variations of the invention may be used and that it is intended that the invention may be practiced otherwise than as specifically described herein. Accordingly, this invention includes all modifications encompassed within the spirit and scope of the invention as defined by the following claims.

What is claimed is:

1. A method for selective synergistic control of broadleaf and grass weeds in a turf site, said method comprising applying an herbicidal composition comprising sulfentrazone and dithiopyr in a ratio of from 1:1 to 1:4, at a rate of from 0.0625 lb/ac to 0.25 lb/ac of sulfentrazone in combination with from 0.125 lb/ac to 0.5 lb/ac of dithiopyr to a locus where weeds are present or are expected to be present.

2. The method of claim 1 wherein the application is pre-emergence and the weeds are selected from the group consisting of crabgrass, chickweed and cudweed.

3. The method of claim 1 wherein the application is post-emergence and the weeds are selected from the group consisting of crabgrass, clover, medic, buckhorn plantain, sorrel and dandelion.

4. The method of claim 1 which comprises applying the individually formulated herbicides, either together or sequentially, to a locus where weeds are present or expected to be present.

* * * * *